United States Patent
Clark et al.

(10) Patent No.: US 11,046,633 B2
(45) Date of Patent: Jun. 29, 2021

(54) CARBONYLATION PROCESS FOR THE PRODUCTION OF METHYL ACETATE

(71) Applicant: Ineos Acetyls UK Limited, Lyndhurst (GB)

(72) Inventors: Thomas Edward Clark, Hull (GB); Nicholas John Hazel, Beverley (GB); John Glenn Sunley, Hull (GB)

(73) Assignee: Ineos Acetyls UK Limited, Lyndhurst (GB)

( * ) Notice: Subject to any disclaimer, the term of this patent is extended or adjusted under 35 U.S.C. 154(b) by 247 days.

(21) Appl. No.: 16/095,125

(22) PCT Filed: Apr. 12, 2017

(86) PCT No.: PCT/EP2017/058770
§ 371 (c)(1),
(2) Date: Oct. 19, 2018

(87) PCT Pub. No.: WO2017/182359
PCT Pub. Date: Oct. 26, 2017

(65) Prior Publication Data
US 2020/0354303 A1    Nov. 12, 2020

(30) Foreign Application Priority Data
Apr. 19, 2016  (GB) .................................... 1606812

(51) Int. Cl.
*C07C 67/37* (2006.01)
*B01J 29/18* (2006.01)
*C07C 69/14* (2006.01)

(52) U.S. Cl.
CPC .............. *C07C 67/37* (2013.01); *B01J 29/18* (2013.01); *C07C 69/14* (2013.01)

(58) Field of Classification Search
CPC ........... C07C 67/37; C07C 69/14; B01J 29/18
See application file for complete search history.

(56) References Cited

U.S. PATENT DOCUMENTS

| | | | |
|---|---|---|---|
| 4,792,620 A * | 12/1988 | Paulik .................. | B01J 31/0231 560/232 |
| 8,394,983 B2 | 3/2013 | Ditzel et al. | |
| 8,809,573 B2 | 8/2014 | Armitage et al. | |
| 9,499,470 B2 | 11/2016 | Ditzel et al. | |
| 9,527,063 B2 | 12/2016 | Hazel et al. | |
| 2010/0063315 A1 | 3/2010 | Ditzel et al. | |
| 2014/0094622 A1 | 4/2014 | Marie-Rose et al. | |

FOREIGN PATENT DOCUMENTS

| | | | | |
|---|---|---|---|---|
| CN | 103896766 A | 7/2014 | | |
| CN | 104689845 A | 6/2015 | | |
| CN | 105188923 A | 12/2015 | | |
| CN | 105339342 A | 2/2016 | | |
| EP | 0596632 A1 | 5/1994 | | |
| WO | 01/07393 A1 | 2/2001 | | |
| WO | 2005/105720 A1 | 11/2005 | | |
| WO | 2006/121778 A1 | 11/2006 | | |
| WO | 2010/061169 A1 | 6/2010 | | |
| WO | WO-2010061169 A1 | * | 6/2010 | ............. C07C 67/37 |
| WO | 2014/135660 A1 | 9/2014 | | |
| WO | 2014/135662 A1 | 9/2014 | | |
| WO | WO-2014135660 A1 | * | 9/2014 | ............. C07C 67/37 |
| WO | WO-2014135662 A1 | * | 9/2014 | .......... B01J 29/7015 |

OTHER PUBLICATIONS

Norskov et al (Nature Chemistry, Towards the Computational Design of Solid Catalysts, 2009, 1, pp. 37-46) (Year: 2009).*
Great Britain Intellectual Property Office Search Report, 1 page, dated Feb. 3, 2017.
Wang et al. "Methyl Acetate Synthesis from Dimethyl Ether Carbonylation over Mordenite Modified by Cation Exchange" J. Phys. Chem. C. 2015, 119, p. 524-533.
International Search Report and Written Opinion for PCT/EP2017/058770 (dated Jun. 6, 2017).
Liu et al, "Carbonylation of Dimethyl Ether during Treatment of ZSM-34 Molecular Sieve Catalyst with Microwave Alkali." Natural Gas Chemical Industry. 2014, vol. 39, p. 14-19.
Xue et al., "Coking on micrometer- and nanometer-sized mordenite during dirnethyl ether carbonylation to methyl acetate." Chinese Journal of Catalysis. 2013, vol. 34, No. 8, p. 1496-1503.

* cited by examiner

*Primary Examiner* — Yevgeny Valenrod
*Assistant Examiner* — Blaine G Doletski
(74) *Attorney, Agent, or Firm* — McDonnell Boehnen Hulbert & Berghoff LLP

(57) ABSTRACT

A process for the production of methyl acetate by carbonylating at a temperature of 250 to 350° C., in the presence of a zeolite catalyst, a feed comprising dimethyl ether, a gas comprising carbon monoxide and hydrogen at a molar ratio of hydrogen to carbon monoxide of at least 1, methyl acetate and one or more compounds containing a hydroxyl functional group.

20 Claims, No Drawings

CARBONYLATION PROCESS FOR THE PRODUCTION OF METHYL ACETATE

This application is a national stage application under 35 U.S.C. § 371 of International Application No. PCT/EP2017/058770, filed Apr. 12, 2017, which claims priority to Great Britain Patent Application No. GB 1606812.4, filed Apr. 19, 2016, the disclosures of which are explicitly incorporated by reference herein.

This invention relates in general to processes for carbonylating dimethyl ether with carbon monoxide in the presence of a zeolite carbonylation catalyst to produce methyl acetate reaction product and, in particular to such carbonylation processes conducted under hydrogen-rich conditions and utilising methyl acetate and one or more compounds containing a hydroxyl functional group as feed components.

Carbonylation processes such as the carbonylation of methanol conducted in the liquid phase in the presence of homogeneous Group VIII metal catalysts to produce acetic acid are operated commercially. Also known are gas phase carbonylation processes employing methanol and/or dimethyl ether using Group VIII metal or zeolite heterogeneous catalysts. Such processes are described in, for example EP-A-0 596 632, WO 01/07393, WO 2005/105720, WO 2006/121778 and WO 2010/061169.

EP-A-0 596 632 describes a vapour phase process for the carbonylation of methanol to produce acetic acid at high temperatures and pressures in the presence of a mordenite catalyst which has been loaded with copper, nickel, iridium, rhodium or cobalt.

WO 01/07393 describes a process for the catalytic conversion of a feedstock comprising carbon monoxide and hydrogen to produce at least one of an alcohol, ether and mixtures thereof and reacting carbon monoxide with the at least one of an alcohol, ether and mixtures thereof in the presence of a catalyst selected from solid super acids, heteropolyacids, clays, zeolites and molecular sieves, in the absence of a halide promoter, under conditions of temperature and pressure sufficient to produce at least one of an ester, acid, acid anhydride and mixtures thereof.

WO 2005/105720 describes a process for production of a carboxylic acid and/or an ester or anhydride thereof by carbonylating an aliphatic alcohol or reactive derivative thereof with carbon monoxide in the substantial absence of halogens at a temperature in the range 250 to 600° C. and a pressure in the range 10 to 200 bar in the presence of a mordenite catalyst which has been modified with copper, nickel, iridium, rhodium or cobalt and has as framework elements, silicon, aluminium, and at least one of gallium, boron and iron.

WO 2006/121778 describes a process for the production of a lower alkyl ester of a lower aliphatic carboxylic acid by carbonylating under substantially anhydrous conditions, a lower alkyl ether such as dimethyl ether, with carbon monoxide in the presence of a mordenite or ferrierite catalyst.

However, it is has been found that in zeolite catalysed carbonylation reactions of dimethyl ether, selectivity to methyl acetate product is generally lower than desirable due to the formation of by-products, and, in particular to the formation of the by-products, methane and $C_{2+}$ hydrocarbons. This problem is addressed in WO 2010/061169.

WO 2010/061169 exemplifies carbonylation reactions of dimethyl ether carried out under carbon monoxide-rich conditions in the presence of copper mordenite (non-templated) catalysts. Methane and $C_{2+}$ hydrocarbon by-product formation is shown to be reduced by employing methyl acetate as a feed component to the reaction.

WO 2014/135660 describes the use of zeolite catalysts which have been calcined at low temperature in processes for the carbonylation of dimethyl ether which processes are carried out utilising a molar ratio of hydrogen to carbon monoxide of at least 1.

WO 2014/135662 describes the use of zeolite catalysts which have been prepared using an organic structure directing agent in processes for the carbonylation of dimethyl ether which are carried out utilising a molar ratio of hydrogen to carbon monoxide of at least 1.

It has now been found that carbonylation reactions of dimethyl ether with carbon monoxide which are carried out utilising methyl acetate as a feed component, a zeolite carbonylation catalyst, and in particular, a templated zeolite carbonylation catalyst, and which are also conducted in the presence of high levels of hydrogen can lead to an undesirable increase in the rate at which the catalyst deactivates thereby reducing the lifetime of the catalyst.

Thus, there remains a need for a carbonylation process which utilises dimethyl ether, carbon monoxide and methyl acetate as feed components and as catalyst, a zeolite carbonylation catalyst, and which process is carried out under conditions of equimolar amounts or greater of hydrogen relative to carbon monoxide, in which the rate of catalyst deactivation is at least maintained and preferably, is reduced. In particular there remains a need for a carbonylation process which utilises dimethyl ether, carbon monoxide and methyl acetate as feed components and as catalyst, a zeolite carbonylation catalyst which catalyst is a templated zeolite catalyst and which process is carried out under conditions of equimolar amounts or greater of hydrogen relative to carbon monoxide, in which the rate of catalyst deactivation is at least maintained and preferably, is reduced It has now been found that in processes for the zeolite catalysed carbonylation of dimethyl ether with carbon monoxide which are conducted using equimolar amounts or greater of hydrogen relative to carbon monoxide and a methyl acetate feed, the rate of catalyst deactivation may be controlled by utilising one or more compounds containing a hydroxyl functional group as a component of the feed to the process.

Accordingly, the present invention provides a process for the carbonylation of dimethyl ether with carbon monoxide in the presence of a catalyst comprising a zeolite to produce a reaction product comprising methyl acetate wherein, the process is carried out at a temperature of from 250 to 350° C., the feed to the process comprises dimethyl ether, carbon monoxide, hydrogen and methyl acetate and the molar ratio of hydrogen to carbon monoxide in the feed is at least 1 and wherein the feed further comprises one or more compounds containing a hydroxyl functional group.

Advantageously, the present invention allows the rate at which the catalyst deactivates to be maintained or reduced thereby providing increased catalyst lifetime.

Thus, the present invention further provides a method of maintaining or reducing the deactivation rate of a catalyst in a process for the carbonylation of dimethyl ether with carbon monoxide in the presence of a catalyst comprising a zeolite to produce a reaction product comprising methyl acetate in which method, the process is carried out at a temperature of from 250 to 350° C., the feed to the process comprises dimethyl ether, carbon monoxide, hydrogen and methyl acetate and the molar ratio of hydrogen to carbon monoxide in the feed is at least 1 and wherein the feed further comprises one or more compounds containing a hydroxyl functional group.

The present invention yet further provides for the use of one or more compounds containing a hydroxyl functional group to maintain or reduce the deactivation rate of a catalyst in a process for the carbonylation of dimethyl ether with carbon monoxide in the presence of a catalyst comprising a zeolite to produce a reaction product comprising methyl acetate wherein the process is carried out at a temperature of from 250 to 350° C., the feed to the process comprises dimethyl ether, carbon monoxide, hydrogen and methyl acetate and the molar ratio of hydrogen to carbon monoxide in the feed is at least 1 and wherein the feed further comprises the one or more compounds containing a hydroxyl functional group.

In some or all embodiments of the present invention, the total amount of hydroxyl compound added to the process is 0.01 to 0.5 mol % based on the total gaseous feed to the process.

In some or all embodiments of the present invention, the process is carried out at a temperature of from 275 to 325° C., such as 280 to 300° C., the molar ratio of hydrogen to carbon monoxide is 1.5 to 4:1 and the one or more hydroxyl compound(s) is present in a total amount of from 0.03 to 0.25 mol %, for example 0.03 to 0.20 mol % based on the total gaseous feed to the process.

In the present invention, dimethyl ether is carbonylated with carbon monoxide in the presence of an at least equimolar amount of hydrogen and a catalyst comprising a zeolite to generate methyl acetate as a reaction product. Methyl acetate is supplied to the process as a component of the feed together with, or separately from one or more compounds containing a hydroxyl functional group. Hereinafter 'the one or more compounds containing a hydroxyl functional group' may be referred to in the specification and claims as 'the hydroxyl compound' or 'the hydroxyl compound(s)' as is appropriate.

The feed components dimethyl ether, carbon monoxide, hydrogen, methyl acetate and the hydroxyl compound(s) can be supplied to the process in gaseous form. If desired, any liquid feed components, such as methyl acetate and the hydoxyl compound(s) may be vaporised, for example in a pre-vapourisation zone, prior to being utilised in the process.

The feed components, dimethyl ether, carbon monoxide, hydrogen, methyl acetate and the hydroxyl compound(s) may be fed to the process as one or more feed streams. The one or more feed streams may each be of a single component or may be a mixture of two or more components. Thus, methyl acetate may be fed to the process as a mixture of methyl acetate and the hydroxyl compound(s) which mixture may also comprise one or more of dimethyl ether, carbon monoxide and hydrogen. Alternatively and/or additionally, methyl acetate may be fed to the process as a separate feed stream to one or more other feed components.

Additional feed components to the process may include inert gases, such as nitrogen, helium and argon.

Suitably, the feed comprises dimethyl ether in an amount of from 1.0 mol % to 20 mol %, for example 1.5 mol % to 15 mol % based on the total gaseous feeds (including recycles) to the process.

Preferably, dimethyl ether for use in the process is substantially pure, that is at least 99% pure dimethyl ether.

Suitably, the feed comprises methyl acetate in an amount of 5 mol % or less based on the total gaseous feeds (including any recycles) to the process, such in an amount of from 0.5 mol % to 5 mol %, for example less than 3 mol %, such as 0.5 to 3 mol %, or for instance in an amount of 2 mol % or less based on the total gaseous feeds (including any recycles) to the process.

Suitably, the feed comprises methyl acetate and dimethyl ether at a molar ratio of methyl acetate to dimethyl ether in the range 1:1 to 100, for example in the range 1:3 to 15.

The feed to the process further comprises one or more hydroxyl compounds.

The hydroxyl compound for use in the present invention is a compound, generally an organic compound which contains a hydroxyl functional group. Suitably, the hydroxyl compound is a compound solely consisting of carbon, hydrogen and oxygen atoms or solely consisting of hydrogen and oxygen atoms. Suitably, the hydroxyl compound is selected from the group consisting of one or more of aliphatic alcohols, aliphatic carboxylic acids, water and mixtures thereof.

Examples of suitable aliphatic alcohols include $C_1$-$C_4$ aliphatic alcohols such as methanol, ethanol, the propanols and the butanols.

Examples of suitable aliphatic carboxylic acids include $C_1$-$C_4$ aliphatic carboxylic acids, such as acetic acid, propionic acid and butanoic acid.

In some or all embodiments of the present invention, the feed comprises one or more hydroxyl compounds selected from one or more of water, acetic acid and methanol.

Suitably, the feed comprises the hydroxyl compound(s) in a total amount of up to 1 mol % based on the total gaseous feeds (including recycles) to the process, for example in a total amount of from 0.01 to 1 mol %, for instance 0.01 to 0.5 mol %, such as 0.01 to 0.2 mol %. If desired, the hydroxyl compound(s) may be added to the process in a total amount of from 0.03 to 0.25 mol %, such as 0.03 to 0.20 mol % based on the total gaseous feed to the process.

Suitably, the feed comprises methyl acetate and the hydroxyl compound(s) at a molar ratio of methyl acetate to hydroxyl compound(s) in the range 500:1 to 0.5:1, for example at a molar ratio in the range 300:1 to 1:1, such as 100 to 4:1.

In some or all embodiments of the present invention, the feed comprises dimethyl ether, carbon monoxide, hydrogen, and methyl acetate in an amount of from 0.5 to 5.0 mol %, and one or more hydroxyl compounds selected from water, acetic acid and methanol in a total amount of from 0.01 to 1.0 mol %, for example 0.03 to 0.5 mol %, such as 0.03 to 0.2 mol %.

In some or all embodiments of the present invention, methyl acetate is present as a component of the feed to the process in an amount of less than 3 mol %, such as less than 2 mol % based on the total gaseous feed to the process and the total amount of the one or more hydroxyl compound(s), preferably selected from water, acetic acid and methanol, is 0.01 to 5 mol %, for example 0.03 to 0.25 mol %, such as 0.03 to 0.20 mol % based on the total gaseous feed to the process. In these embodiments, the process is preferably carried out at a temperature of from 275 to 325° C. and at a molar ratio of hydrogen to carbon monoxide in the range 1.5 to 4:1.

The process is carried out utilising carbon monoxide and hydrogen at a molar ratio of hydrogen to carbon monoxide of at least 1. For the avoidance of doubt, the phrase 'a molar ratio of hydrogen to carbon monoxide of at least 1' means that the molar ratio of hydrogen/carbon monoxide is at least 1. Suitably, the molar ratio of hydrogen to carbon monoxide is in the range 1 to 12:1, for example 1 to 8:1, such as 1 to 4:1, for instance 1.5 to 4:1.

The carbon monoxide may contain impurities that do not interfere with the conversion of the dimethyl ether to methyl acetate product, such as nitrogen, helium, argon, methane and/or carbon dioxide.

Suitably, synthesis gas may be utilised as the source of carbon monoxide and hydrogen to the process. Synthesis gas and processes for the commercial production of such is well known to the skilled person in the art. Typical production processes for the manufacture of synthesis gas include the reforming or the partial oxidation of hydrocarbons such as methane. Synthesis gas comprises a mixture of carbon monoxide and hydrogen and may also comprise some carbon dioxide.

Thus, the feed to the process of the present invention may additionally comprise carbon dioxide, for example in an amount of 50 mol % or less, such as 0.5 to 12 mol %.

The process utilises a catalyst which comprises a zeolite. Zeolites are crystalline aluminosilicates which have framework structures constructed from tetrahedra of $SiO_4$ and $AlO_4$ that share vertices. Each framework topology contains a regular array of pores, channels and/or pockets that vary in size, shape and dimensionality. These framework topologies or structure types of zeolites are assigned three-letter structure codes by the Structure Commission of the International Zeolite Association, under the authority of IUPAC. A description of zeolites, their structure, properties and methods of synthesis can be found in The Atlas of Zeolite Framework Types (C. Baerlocher, W. M. Meier, D. H. Olson, 5$^{th}$ Ed. Elsevier, Amsterdam, 2001) in conjunction with the web-based version (http://www.iza-structure.org/databases/).

A zeolite for use in the process should be effective to catalyse the carbonylation of dimethyl ether to produce a reaction product comprising methyl acetate. Suitable zeolites have at least one channel or pocket (hereinafter collectively referred to as channels) which is defined by an 8-member ring. Preferably, the 8-member ring channel is interconnected with at least one channel defined by a ring with 10 or 12 members. The window size of the zeolite channel systems should be such that the reactant dimethyl ether and carbon monoxide molecules can diffuse freely in and out of the zeolite framework. Suitably, the window size of an 8-member ring channel or pocket is at least 2.5×3.6 Angstroms.

In some or all embodiments of the present invention, the catalyst is a zeolite having a framework type selected from the group consisting of MOR, FER, OFF, CHA, GME, MFS, EON and ETR.

Examples of zeolites of framework type MOR include mordenite. Examples of zeolites of framework type FER include ferrierite and ZSM-35. Examples of zeolites of framework type OFF include offretite. Examples of zeolites of framework type CHA include chabazite. Examples of zeolites of framework type GME include gmelinite. Examples of zeolites of framework type MFS include ZSM-57. Examples of zeolites of framework type EON include ECR-1. Examples of zeolites of framework type ETR include ECR-34.

In some or all embodiments of the present invention, the catalyst is a zeolite of framework type MOR and is mordenite, for example mordenite in hydrogen form or in an ammonium form, preferably mordenite in a hydrogen form.

In addition to the framework elements silicon and aluminium, the zeolite, for example mordenite, may have additional elements in its framework, such as at least one of gallium, boron and iron.

Applicant has found that in carbonylation processes of dimethyl ether conducted in the presence of an equimolar or excess amount of hydrogen relative to carbon monoxide, the use of a templated zeolite can provide improved catalytic performance compared to the use of equivalent but non-templated zeolites. However, whilst the use of templated zeolite catalysts under hydrogen-rich process conditions may provide improved catalytic activity, Applicant has surprisingly found that under these hydrogen-rich conditions the templated zeolite catalyst may exhibit an increased rate of deactivation. However, and advantageously, utilisation of the hydroxyl compound(s) of the present invention can lead to an improvement in catalyst deactivation rate in carbonylation processes of dimethyl ether conducted under conditions of at least equimolar amounts of hydrogen relative to carbon monoxide and which processes also utilise a catalyst comprising a templated zeolite.

By 'templated zeolite' is meant throughout this specification and in the claims a zeolite which has been prepared from a synthesis mixture which comprises one or more organic structure directing agents.

In some or all embodiments of the present invention, the catalyst is a templated zeolite, for example a templated mordenite or a templated ferrierite. Suitably, a templated mordenite or templated ferrierite is utilised in the carbonylation process in a hydrogen form or it may be utilised in a metal loaded form, such as a copper mordenite or silver mordenite.

Templated zeolites such as templated mordenites and ferrierites are available commercially or they may be synthesised using well known preparation techniques.

Suitably, a templated zeolite may be prepared from a synthesis mixture comprising a source of silica, a source of alumina, a source of alkali or alkaline earth metal, water and at least one organic structure directing agent.

The selection of the organic structure directing agent is dependent upon the desired zeolite structure to be achieved. Suitably, for use in the present invention a templated zeolite may be synthesised using one or more organic structure directing agents which are basic nitrogen compounds, such as primary amines, secondary amines, tertiary amines, salts and bases of quaternary ammonium compounds and heterocyclic nitrogen compounds. These compounds may be aliphatic or aromatic.

In some or all embodiments of the present invention a templated zeolite, for example a templated mordenite, may be prepared from a synthesis mixture which comprises silica, for example fumed silica, a water soluble aluminate, for example sodium aluminate, an alkali metal hydroxide, for example sodium hydroxide, and an organic structure directing agent, for example a quaternary ammonium compound, such as an aliphatic quatemary ammonium compound, for example a tetralkylammonium compound, in particular a tetraethylammonium compound and more particularly a tetralkylammonium halide, for example tetraethylammonium bromide, water and optionally a source of gallium oxide.

In order to maintain a predetermined composition in the templated zeolite it will generally be preferable to employ starting materials of known purity and composition so that composition control is maintained.

The components are brought together in defined proportions in water to compose a zeolite-forming aqueous synthesis mixture. The synthesis mixture is hydrothermally treated (with or without pressure) for a time and at a temperature to promote crystallisation.

Suitably, the synthesis mixture is maintained until crystals of the zeolite are formed, for example for a period of from 6 to 500 hours at elevated temperature, for example at a temperature of 80° C. to 210° C. At lower temperatures, for example 80° C., the crystallisation time is longer. Hydrothermal conditions found to be particularly suitable are a temperature of 150° C. to 170° C. for a period of about 3 to 14 days with agitation, for example with stirring, rotation or tumbling.

Crystallisation of the synthesis mixture may be performed with or without pressure but is suitably performed under pressure, for example in a stirred or tumbled autoclave. The resulting crystalline zeolite is then separated from the liquid and recovered, for example by filtration, washing with water, suitably with deionised or distilled water and dried. The synthetic zeolite crystallises as a fine powder which exhibits an x-ray diffraction pattern characteristic of that particular type of zeolite.

The proportions of the components of the synthesis mixture can be adjusted to produce the desired templated zeolite. In the case of mordenite, the following molar ratios, expressed as oxide ratios, of synthesis mixture components may be employed:—

$SiO_2/M_2O_3$ from 10 to 100, preferably 20 to 60
$H_2O/Al_2O_3$ from 500 to 3000
$OSDA/Al_2O_3$ from 1 to 15
$Na_2O/A_2O_3$ from 1 to 15, for example 1 to 10 wherein M is a trivalent metal selected from one or more of Al, Ga, B and Fe; OSDA is the organic structure directing agent, suitably a basic nitrogen compound.

As a result of the crystallisation process, the recovered template zeolite contains within its pores the organic structure directing agent used in the synthesis mixture. Desirably, the organic structure directing agent is removed or substantially removed from within the pores of the zeolite prior to its use in the present invention. A variety of removal methods may be used including combustion or by thermal treatment. In general, at least 50% of the organic structure directing agent is removed, and preferably essentially all the organic structure directing agent is removed.

A preferred method of removal is by a thermal treatment, such as calcination, which may be carried out, for example at temperatures ranging from about 300° C. to about 650° C. Calcination may take place in the presence of an inert atmosphere, such as nitrogen or an oxidising atmosphere such as oxygen or air for a period of time ranging from about 1 to about 9 hours or longer.

If desired, the zeolite may be utilised in the carbonylation process in an ammonium or hydrogen form. Thus, an as-synthesised zeolite may be treated to reduce its alkali and alkaline earth metal content by conventional ion exchange procedures with replacing cations. In general, ion exchange is conducted with an aqueous solution of replacing cations, such as an aqueous solution of ammonium ions at temperatures of from about 25° C. to about 100° C. for a suitable time interval, for example about 1 to 6 hours. The degree of the ion-exchange can be varied by changing the time of the contact, concentration of the replacing cation solution and temperature.

Following contact with an aqueous salt solution of the desired replacing cation, the zeolite may be washed with water and dried to produce a dry zeolite having the replacing cations occupying the alkali/alkaline earth metal sites.

The ammonium form of a zeolite may readily be converted to its hydrogen form by calcination, for example at temperatures in the range 300° C. to 650° C. Calcination causes the ammonium ion to decompose leaving the structure in a hydrogen form.

Suitably, the catalyst is a zeolite, preferably a templated zeolite, which is in its hydrogen form.

As-synthesised zeolites are fine crystalline powders. Since a powder has no significant mechanical strength, its practical applications are limited. Mechanical strength can be conferred on a zeolite, such as by forming the zeolite into shaped particles. Processes for forming zeolites into shaped particles are well-known in the art and may be accomplished by forming a gel or paste of the zeolite powder with the addition of a suitable binder such as a clay or an inorganic oxide, and then extruding the gel or paste into the desired shape and then dried. The resultant extrudate may also be calcined, for example at temperatures of at least 450° C. Thus, suitably, the catalyst for use in the present invention is a zeolite which is composited with at least one binder material. Examples of suitable binder materials include inorganic oxides, such as silicas, aluminas, alumina-silicates, magnesium silicates, magnesium aluminium silicates, titanias and zirconias.

Preferred binder materials include aluminas, alumina-silicates and silicas, for example boehemite type alumina.

The relative proportions of zeolite and the binder material in a composite may vary widely but suitably the binder material may be present in an amount in the range of 10% to 90% by weight of the composite.

Zeolite powders may also be formed into particles without the use of a binder. Typical zeolite particles include extrudates whose cross-sections are circular or embrace a plurality of arcuate lobes extending outwardly from the central portion of the zeolite particles.

Prior to its use in the carbonylation process, the catalyst is preferably dried. The catalyst may be dried by any suitable means, for example by heating to a temperature of from 60° C. to 500° C.

The silica to alumina molar ratio of zeolites for use in the carbonylation process is the bulk or overall ratio. This can be determined by any one of a number of chemical analysis techniques. Such techniques include x-ray fluorescence, atomic absorption and ICP (inductive coupled plasma). All will provide substantially the same silica to alumina molar ratio value.

The bulk silica to alumina molar ratio of synthetic zeolites will vary. For example, the silica to alumina molar ratio of a zeolite, such as mordenite may range from as low as 5 to over 90. Suitably, for use in the present invention, the silica to alumina molar ratio of a zeolite is in the range from 10 to 90, for example 10 to 60, such as in the range 20 to 40.

In some or all embodiments of the present invention, the zeolite is a mordenite zeolite, preferably a templated mordenite, wherein the mordenite has a silica to alumina ratio of at least 5 but, preferably less than or equal to 100, such as in the range 6 to 90, for example 10 to 40.

The carbonylation process is carried out at temperatures of from 250° C. to 350° C. Suitably, the process is carried out at a temperature of from 275 to 325° C., for example 280 to 320° C., such as 280 to 300° C.

Suitably, the carbonylation process is carried out at pressures of from 1 to 100 barg, for example at pressures of from 50 to 100 barg.

In some or all embodiments of the present invention, the carbonylation process is carried out at a temperature of from 275° C. to 325° C., such as 280 to 320° C., for example 280 to 300° C. and at a pressure of from 50 to 100 barg.

The carbonylation process may be carried out at a Gas Hourly Space Velocity (GHSV) in the range 500 to 40,000 h$^{-1}$, for example in the range 2000 to 10,000 h$^{-1}$.

In some or all embodiments of the present invention, the carbonylation process is carried out at a temperature of from 275° C. to 325° C., a pressure of from 50 to 100 barg and a GHSV in the range 2000 to 10,000 h$^{-1}$.

The process may be carried out using one or more beds of catalysts, suitably selected from fixed bed, fluidised bed and moving beds of catalyst.

The reaction product of the carbonylation process comprises methyl acetate and it may also comprise acetic acid and unconverted reactants such as dimethyl ether and carbon monoxide.

Desirably, methyl acetate is recovered from the reaction product. In general, the reaction product is withdrawn from the process as a vapour stream which may be cooled and condensed to recover a methyl acetate-rich liquid stream. Typically, the methyl acetate-rich liquid stream comprises predominantly methyl acetate but may also comprise minor amounts of one or more of unreacted dimethyl ether, water and dissolved inert gases. Methyl acetate may be recovered from the methyl acetate-rich liquid stream, for example by distillation and the recovered methyl acetate sold as such or used as a feedstock in downstream chemical processes.

Suitably, some or all of the recovered methyl acetate may be converted to acetic acid, preferably by a hydrolysis process. Hydrolysis of the recovered methyl acetate may be carried out using any suitable process, such as by catalytic distillation. Typically, in catalytic distillation processes for the hydrolysis of methyl acetate, methyl acetate is hydrolysed with water in a fixed-bed reactor employing an acidic catalyst, such as an acidic ion exchange resin or a zeolite catalyst to produce a mixture comprising acetic acid and methanol from which acetic acid and methanol may be separated by distillation, in one or more distillation stages.

The carbonylation process may be operated as either a continuous or a batch process, preferably as a continuous process.

The invention is now illustrated with reference to the following non-limiting Examples.

EXAMPLE 1

This Example demonstrates carbonylation of dimethyl ether with carbon monoxide in the presence of a templated zeolite catalyst under hydrogen-rich conditions and utilising feeds comprising (i) methyl acetate and water or acetic acid and (ii) methyl acetate.

The carbonylation reactions were conducted in a reactor (length 1215 mm and internal diameter 20.4 mm) containing a 137.4 mL bed of templated mordenite catalyst in the form of 3.2 mm diameter extrudates. The temperature of the catalyst bed was determined from thermocouples positioned at a number of points within the bed.

A gaseous feed stream of 9 mol % dimethyl ether, carbon monoxide and hydrogen at a molar ratio of 1:4 and 2.97 mol % methyl acetate doped with water (so as to provide a water concentration of 0.03 mol % in the total feed) ("water-doped feed") was supplied to the reactor under reaction conditions of a pressure of 70 barg (7000 kPa), a temperature of 283° C. and a gas hourly space velocity of 4000 h$^{-1}$ for a period of 264 hours (Period A). Following Period A, the water-doped feed was replaced by a feed of 3 mol % methyl acetate containing essentially no water ("non-doped feed") and the reaction was allowed to continue under these conditions for a period of 96 hours (Period B). Following Period B, the non-doped feed was replaced by the water-doped feed and the reaction was allowed to continue under these conditions for 192 hours (Period C). Following Period C, the water-doped feed was replaced with the non-doped feed and the reaction was allowed to continue under these conditions for 120 hours (Period D). Following Period D, the non-doped feed was replaced by a 2.97 mol % methyl acetate feed doped with acetic acid (so as to provide an acetic acid concentration of 0.03 mol % in the total feed) ("acid-doped feed") and the reaction was allowed to continue under these conditions for 200 hours (Period E).

The effluent stream from the reactor was periodically analysed on two Varian gas chromatographs to determine the concentration of carbonylation reactants and products. The first gas chromatograph was equipped with two FID detectors and the second gas chromatograph was fitted with two TCD detectors.

The results of the experiments are shown in Tables 1 and 2 below. The rate of deactivation of the catalyst was determined by the change (° C. loss per day) in the average internal catalyst bed temperature.

TABLE 1

| Time Period | Hydroxyl compound | Catalyst deactivation rate (° C. loss per day) |
|---|---|---|
| A | water | 0.00 |
| B | none | 0.22 |
| C | water | 0.00 |
| D | none | 0.18 |
| E | acetic acid | 0.01 |

As can be seen from the results in Table 1, the catalyst deactivation rates in the carbonylation reactions conducted with feeds containing a hydroxyl compound were significantly reduced compared to the deactivation rates using feeds which did not contain a hydroxyl compound.

The results in Table 2 show the impact of using feeds with and without hydroxyl compounds on the production of by-product methane in the reactions of Example 1.

TABLE 2

| Time Period | Hydroxyl compound | Methane STY (gLcat$^{-1}$h$^{-1}$) |
|---|---|---|
| A | water | 6.0 |
| B | none | 4.0 |
| C | water | 5.5 |
| D | none | 3.5 |
| E | acetic acid | 4.0 |

EXAMPLE 2

Using the apparatus and 91.6 mL catalyst as described in Example 1 above, a gaseous carbonylation feed of carbon monoxide and hydrogen at a molar ratio of 1:4, 9 mol % dimethyl ether and 0.94 mol % methyl acetate doped with acetic acid (so as to provide an acetic acid concentration of 0.06 mol % in the total feed) was fed to the reactor under reaction conditions of a pressure of 70 barg (7000 kPa), a temperature of 286° C. and a gas hourly space velocity of 6000 h$^{-1}$ for 350 hours (Period A). After Period A, the methyl acetate doped feed was changed to a feed of 1.88 mol % methyl acetate doped with acetic acid (so as to provide an acetic acid concentration of 0.12 mol % in the total feed) and the reaction was allowed to continue under these conditions for 161 hours (Period B). After Period B, the methyl acetate doped feed was changed to a feed of 0.88 mol % methyl acetate doped with acetic acid (so as to provide an acetic acid concentration of 0.12 mol % in the total feed) and the reaction was allowed to continue under these conditions (Period C).

The results of the experiments are shown in Table 3 below. Deactivation rates of the catalyst were determined by the change (° C. loss per day) in the average internal catalyst bed temperature. The amounts of feed components in the Table are based on the total feed to the reactor.

TABLE 3

| Time Period | Amount of methyl acetate (mol %) | Amount of acetic acid (mol %) | Catalyst deactivation rate (° C. loss per day) |
|---|---|---|---|
| A | 0.94 | 0.06 | 0.08 |
| B | 1.88 | 0.12 | 0.00 |
| C | 0.88 | 0.12 | 0.00 |

The results in Table 3 demonstrate that the deactivation rate of a templated zeolite catalyst, utilised in reactions for the carbonylation of dimethyl ether carried out under hydrogen-rich conditions, can be effectively maintained by utilising acetic acid as a component of the reaction feed. The methyl acetate concentration used in Period C was reduced by approximately half of that used in Period B. No detrimental effect was observed to the catalyst deactivation rate in Period C. This demonstrates that use of acetic acid as a component of a carbonylation reaction feed is beneficial to maintaining catalyst deactivation rate and consequently, catalyst lifetime.

EXAMPLE 3

Using the apparatus and 91.6 mL catalyst as described in Example 1 above, a gaseous carbonylation feed of carbon monoxide and hydrogen in a molar ratio of 1:4, 9 mol % dimethyl ether and 0.81 mol % methyl acetate doped with acetic acid (so as to provide an acetic acid concentration of 0.19 mol % in the total feed) was supplied to the reactor under reaction conditions of a pressure of 70 barg (7000 kPa), a temperature of 286° C. and a gas hourly space velocity of 6000 h$^{-1}$ for 80 hours (Period A). Following Period A, the hydrogen:carbon monoxide molar ratio was changed to a molar ratio of 2.5H$_2$:1CO and the reaction was allowed to continue under these conditions for 317 hours (Period B). Following Period B, the acid-doped methyl acetate feed was replaced by a feed of 0.81 mol % methyl acetate doped with methanol (so as to provide a methanol concentration of 0.19 mol % in the total feed) and the reaction allowed to continue under these conditions for a period of 60 hours (Period C). The deactivation rate of the catalyst was determined by the change (° C. loss per day) in the average internal catalyst bed temperature. The results of Example 3 are shown in Table 4 below.

TABLE 4

| Time Period | Hydroxyl compound | H$_2$:CO molar ratio | Catalyst deactivation rate (° C. loss per day) |
|---|---|---|---|
| A | acetic acid | 4:1 | 0.00 |
| B | acetic acid | 2.5:1 | 0.11 |
| C | methanol | 2.5:1 | 0.00 |

The results in Table 4 demonstrate that in Example 3 the use of methanol reduces the rate at which the catalyst deactivates more effectively than acetic acid.

EXAMPLE 4

Using the apparatus and 109.9 mL of catalyst as described in Example 1 above, a gaseous carbonylation feed of carbon monoxide and hydrogen in a molar ratio of 1:1.75, 9 mol % dimethyl ether and 0.81 mol % methyl acetate doped with methanol (so as to provide a methanol concentration of 0.19 mol % in the total feed) was supplied to the reactor under reaction conditions of a pressure of 70 barg (7000 kPa), a temperature of 283° C. and a gas hourly space velocity of 5000 h for a period of 1040 hours (Period A). After Period A, the methanol-doped methyl acetate feed was changed to a feed of 0.81 mol % methyl acetate feed doped with acetic acid (so as to provide an acetic acid concentration of 0.19 mol % in the total feed) and the reaction was allowed to continue under these conditions for 46 hours (Period B). After Period B, the doped methyl acetate feed to the reactor was ceased and the reaction allowed to continue in the absence of the methyl acetate doped feed for a period of 114 hours (Period C). The deactivation rate of the catalyst was determined by the change (° C. loss per day) in the average internal catalyst bed temperature. The results of Example 4 are shown in Table 5 below.

TABLE 5

| Time Period | Hydroxyl compound | Catalyst deactivation rate (° C. loss per day) |
|---|---|---|
| A | methanol | 0.00 |
| B | acetic acid | 0.06 |
| C | none | 0.83 |

The results in Table 5 demonstrate that the rate of catalyst deactivation is reduced if methanol or acetic acid is present as a component of the feed to the carbonylation reaction.

EXAMPLE 5

Using the apparatus and 110.0 mL catalyst as described in Example 1 above, a gaseous carbonylation feed of carbon monoxide and hydrogen at a molar ratio of 1:1.8, 9 mol % dimethyl ether and 0.85 mol % methyl acetate doped with acetic acid (so as to provide an acetic acid concentration of 0.15 mol % in the total feed) was supplied to the reactor under reaction conditions of a pressure of 70 barg (7000 kPa), a temperature of 280° C. and a gas hourly space velocity of 5000 h$^{-1}$ for a period of 1057 hours (Period A). After Period A, the methyl acetate doped feed was changed to 0.80 mol % methyl acetate doped with acetic acid (so as to provide acetic acid at a concentration of 0.20 mol % based on the total feed), the temperature was increased to 297.5° C. and the reaction was allowed to continue under these conditions for 840 hours (Period B). After Period B, the methyl acetate doped feed was maintained but the temperature was increased to 299.5° C. and the reaction was allowed to continue under these conditions for 52 hours (Period C). After Period C, the methyl acetate doped feed was changed to 0.80 mol % methyl acetate doped with methanol (so as to provide methanol at a concentration of 0.20 mol % based on the total feed), the temperature was increased to 301.5° C. and the reaction was allowed to continue under these conditions for 106 hours (Period D). After Period D, the methyl acetate doped feed was changed to 0.90 mol % methyl acetate doped with water (so as to provide water at a concentration of 0.10 mol % based on the total feed), the temperature was increased to 312.0° C. and the reaction was allowed to continue under these conditions for 110 hours (Period E). After Period E, the methyl acetate doped feed was changed to 0.82 mol % methyl acetate doped with water, acetic acid and methanol (so as to provide water, acetic acid and methanol at a concentration of 0.02, 0.01 and 0.15 mol % respectively based on the total feed), the temperature was maintained at 312° C. and the reaction was allowed to continue under these conditions for 30 hours (Period F).

The deactivation rate of the catalyst was determined by the change (° C. loss per day) in the average internal catalyst bed temperature. The results of Example 5 are shown in Table 6 below.

TABLE 6

| Time Period | Amount of methyl acetate (mol %) | Hydroxyl Compound | Amount of hydroxyl compound (mol %) | Catalyst deactivation rate (° C. loss per day) |
|---|---|---|---|---|
| A | 0.85 | acetic acid | 0.15 | 0.02 |
| B | 0.80 | acetic acid | 0.20 | 0.01 |
| C | 0.80 | acetic acid | 0.20 | 0.00 |
| D | 0.80 | methanol | 0.20 | 0.02 |
| E | 0.90 | water | 0.10 | 0.00 |
| F | 0.82 | water, methanol and acetic acid | 0.18 | 0.03 |

The results in Table 6 demonstrate that the deactivation rate of the catalyst can be effectively maintained by adding to the process any one of acetic acid, methanol, water or a mixture thereof.

EXAMPLE 6

This example was carried out using a stainless steel pipe reactor of 0.4 mm internal diameter containing a 2.0 mL bed of 3.2 mm diameter templated mordenite catalyst extrudates with any interstitial voids filled with ceramic beads. The reactor was heated to the desired reaction temperature and pressurised to 70 barg (7000 kPa).

A gaseous feed of 9 mol % dimethyl ether, 0.85 mol % methyl acetate doped with acetic acid to provide a concentration of 0.15 mol % acetic acid in the total feed, 5 mol % helium and carbon monoxide and hydrogen in a molar ratio of 1:2.5 was supplied to the reactor at a gas hourly space velocity of 4000 h$^{-1}$ for 192 hours (Period A) under the reaction conditions of 300° C. and 70 barg (7000 kPa).

After Period A, the methyl acetate doped feed was switched off and the carbonylation reaction was allowed to continue at 300° C. and 70 barg (7000 kPa) for a period of 79 hours (Period B).

The gaseous effluent stream from the reactor was diluted with 200 mL/min nitrogen, reduced to atmospheric pressure and periodically analysed during Periods A and B, using two Agilent gas chromatographs, to determine the concentration of carbonylation reactants and products. The first chromatograph was equipped with two FID detectors and the second with two TCD detectors.

The deactivation rate of the catalyst was determined by the % change in the acetyls STY (gLcat$^{-1}$ h$^{-1}$) per day. A negative % STY change per day indicates that the catalyst is deactivating.

The results of this Example are shown in Table 7 below.

TABLE 7

| Period | Hydroxyl compound | Deactivation Rate (% STY change per day) |
|---|---|---|
| A | acetic acid | 0.0 |
| B | none | −4.5 |

The results in Table 7 demonstrate that during Period B when no acetic acid was present, the catalyst was deactivating whereas in Period A, the catalyst was found to be stable. These results show that the presence of acetic acid in the carbonylation feed mitigates catalyst deactivation.

EXAMPLE 7

Using the reactor as described above in Example 6, Example 6 was repeated except that the gaseous feed to the reactor had 0.80 mol % methyl acetate doped with methanol to provide a concentration of 0.20 mol % methanol in the total feed, and the reaction was carried out at a temperature of 292° C. The results of Example 7 are shown in Table 8 below.

TABLE 8

| Period | Hydroxyl compound | Deactivation Rate (% STY change per day) |
|---|---|---|
| A | methanol | 0.0 |
| B | none | −3.3 |

The results in Table 8 demonstrate that during Period B when methanol was not used as a component of the feed, the catalyst was deactivating whereas in Period A, the catalyst was found to be stable. These results show that the presence of methanol in the carbonylation feed mitigates catalyst deactivation.

EXAMPLE 8

Using the reactor as described above in Example 6, Example 6 was repeated except that the gaseous feed to the reactor had 0.90 mol % methyl acetate doped with water to provide a concentration of 0.10 mol % water in the total feed, and the reaction was carried out at a temperature of 297° C. The results of Example 8 are shown in Table 9 below.

TABLE 9

| Period | Hydroxyl compound | Deactivation Rate (% STY change per day) |
|---|---|---|
| A | water | 0.0 |
| B | none | −2.9 |

The results in Table 9 demonstrate that during Period B when water was not used as a component of the feed, the catalyst was deactivating whereas in Period A, the catalyst was found to be stable. These results show that the presence of water in the carbonylation feed mitigates catalyst deactivation.

The invention claimed is:

1. A process for the carbonylation of dimethyl ether with carbon monoxide in the presence of a catalyst comprising a templated zeolite to produce a reaction product comprising methyl acetate wherein the process is carried out at a temperature of from 250 to 350° C., the feed to the process comprises
- dimethyl ether,
- carbon monoxide,
- hydrogen,
- methyl acetate, and
- one or more hydroxyl compound(s) selected from water, a $C_1$-$C_4$ aliphatic alcohol, and a $C_1$-$C_4$ aliphatic carboxylic acid;

the molar ratio of hydrogen to carbon monoxide in the feed is at least 1, and the molar ratio of methyl acetate to the one or more hydroxyl compound(s) is in the range 500:1 to 0.5:1.

2. The process according to claim 1 wherein the feed comprises the hydroxyl compound(s) in a total amount of up to 1 mol % based on a total gaseous feed to the process including the hydroxyl compound(s), dimethyl ether, carbon monoxide, hydrogen, and methyl acetate.

3. The process according to claim 1 wherein the feed comprises the hydroxyl compound(s) in a total amount of 0.01 to 0.5 mol % based on a total gaseous feed to the process including the hydroxyl compound(s), dimethyl ether, carbon monoxide, hydrogen, and methyl acetate.

4. The process according to claim 1, wherein the feed comprises methyl acetate and the hydroxyl compound(s) at a molar ratio of methyl acetate to hydroxyl compound(s) in the range 300:1 to 1:1.

5. The process according to claim 1, wherein the hydroxyl compound is water.

6. The process according to claim 1 wherein the hydroxyl compound is a $C_1$-$C_4$ aliphatic alcohol.

7. The process according to claim 1 wherein the hydroxyl compound is a $C_1$-$C_4$ aliphatic carboxylic acid.

8. The process according to claim 1 wherein the hydroxyl compound is selected from one or more of water, acetic acid and methanol.

9. The process according to claim 1, wherein the feed comprises hydrogen and carbon monoxide at a molar ratio of hydrogen to carbon monoxide in the range 1.5 to 4:1.

10. The process according to claim 1, wherein the feed comprises methyl acetate in an amount up to 5 mol % based on a total gaseous feed to the process including the hydroxyl compound(s), dimethyl ether, carbon monoxide, hydrogen, and methyl acetate.

11. The process according to claim 1, wherein the catalyst is a zeolite having at least one channel which is defined by an 8-membered ring.

12. The process according to claim 11 wherein the zeolite has a framework type selected from the group consisting of MOR, FER, OFF, CHA, GME, MFS, EON and ETR.

13. The process according to claim 12 wherein the zeolite has the framework type MOR and is mordenite.

14. The process according to claim 1, wherein the process is carried out at a temperature of from 275 to 325° C.

15. The process according to claim 1, wherein methyl acetate product is hydrolysed to acetic acid.

16. A method of maintaining or reducing the deactivation rate of a catalyst in a process for the carbonylation of dimethyl ether with carbon monoxide in the presence of a catalyst comprising a templated zeolite to produce a reaction product comprising methyl acetate in which method, the process is carried out at a temperature of from 250 to 350° C., the feed to the process comprises dimethyl ether, carbon monoxide, hydrogen, methyl acetate, and one or more hydroxyl compound(s) selected from water, a $C_1$-$C_4$ aliphatic alcohol, and a $C_1$-$C_4$ aliphatic carboxylic acid, the molar ratio of hydrogen to carbon monoxide in the feed is at least 1, and the molar ratio of methyl acetate to the one or more hydroxyl compound(s) is in the range 500:1 to 0.5:1.

17. The process according to claim 1, wherein the feed to the process includes one or more gaseous recycles, and the feed comprises methyl acetate in an amount up to 5 mol % based on a total gaseous feed, including gaseous recycles, to the process including the hydroxyl compound(s), dimethyl ether, carbon monoxide, hydrogen, and methyl acetate.

18. The process according to claim 1, wherein the feed comprises methyl acetate and the hydroxyl compound(s) at a molar ratio of methyl acetate to hydroxyl compound(s) in the range 100:1 to 4:1.

19. The process according to claim 1, wherein the feed comprises
- methyl acetate, present in an amount of from 0.5 to 5.0 mol %; and
- one or more hydroxyl compounds selected from water, acetic acid, and methanol, present in a combined amount of from 0.03 to 0.5 mol %.

20. The process according to claim 1, wherein
methyl acetate is present in the feed in an amount of less than 2 mol %;
one or more of water, acetic acid and methanol are present in the feed in a combined amount of from 0.03 to 0.2 mol %;
hydrogen and carbon monoxide are present in the feed in a molar ratio in the range 1.5:1 to 4:1; and
the process is carried out at a temperature of from 275 to 325° C.

* * * * *